US012246016B2

(12) United States Patent
Surrallés Calonge et al.

(10) Patent No.: US 12,246,016 B2
(45) Date of Patent: Mar. 11, 2025

(54) THERAPEUTIC USE OF AFATINIB IN CANCER

(71) Applicants: UNIVERSITAT AUTÒNOMA DE BARCELONA, Barcelona (ES); CONSORCIO CENTRO DE INVESTIGACIÓN BIOMÉDICA EN RED, M.P., Madrid (ES); FUNDACIÓ INSTITUT DE RECERCA DE L'HOSPITAL DE LA SANTA CREU I SANT PAU, Barcelona (ES)

(72) Inventors: Jordi Surrallés Calonge, Barcelona (ES); Jordi Minguillón Pedreño, Barcelona (ES); Helena Montanuy Escribano, Barcelona (ES)

(73) Assignees: UNIVERSITAT AUTÒNOMA DE BARCELONA, Bellaterra (ES); CONSORCIO CENTRO DE INVESTIGACIÓN BIOMÉDICA EN RED, M.P, Bellaterra (ES); FUNDACIÓ INSTITUT DE RECERCA DE L'HOSPITAL DE LA SANTA CREU I SANT PAU, Barcelona (ES)

( * ) Notice: Subject to any disclaimer, the term of this patent is extended or adjusted under 35 U.S.C. 154(b) by 936 days.

(21) Appl. No.: 17/260,990

(22) PCT Filed: Jul. 15, 2019

(86) PCT No.: PCT/EP2019/069039
§ 371 (c)(1),
(2) Date: Jan. 15, 2021

(87) PCT Pub. No.: WO2020/016191
PCT Pub. Date: Jan. 23, 2020

(65) Prior Publication Data
US 2021/0290622 A1 Sep. 23, 2021

(30) Foreign Application Priority Data
Jul. 16, 2018 (EP) .................................. 18382527

(51) Int. Cl.
*A61K 31/517* (2006.01)
*A61P 35/00* (2006.01)
(52) U.S. Cl.
CPC ............ *A61K 31/517* (2013.01); *A61P 35/00* (2018.01)
(58) Field of Classification Search
CPC ............................. A61K 31/517; A61P 35/00
See application file for complete search history.

(56) References Cited

FOREIGN PATENT DOCUMENTS

WO WO2016001844 A1 1/2016
WO WO 2017/021857 A1 2/2017

OTHER PUBLICATIONS

International Search Report and Written Opinion mailed on May 17, 2019 for Application No. PCT/EP2019/069039, 13 pages.
Avlasevich, et al: "Flow cytometric analysis of micronuclei in mammalian cell cultures: past, present and future", 2011, Mutagenesis 2011; vol. 26, pp. 147-152.
Bryce, et al: "In vitro micronucleus assay scored by flow cytometry provides a comprehensive evaluation of cytogenetic damage and cytotoxicity", 2007, Mutat. Res. 2007, Toxicol. Environ. Mutagen., vol. 630, pp. 78-91.
Jia, et al: "Successful treatment of a patient with Li-Fraumeni syndrome and metastatic lung adenocarcinoma harboring synchronous EGFR L858R and ERBB2 extracellular domain S310F mutations with the pan-HER inhibitor afatinib", Cancer Biology & Therapy; Aug. 19, 2014; vol. 15, No. 8, pp. 970-974; doi:10.4161/cbt.29173.
Río, et al: "In vitro phenotypic correction of hematopoietic progenitors from Fanconi anemia group A knockout mice", Blood 2002, Gene Therapy; vol. 100, No. 6, pp. 2032-2039.
Specenier, et al: "Afatinib in squamous cell carcinoma of the head and neck", Expert Opinion on Pharmacotherapy, May 19, 2016; vol. 17, No. 9, pp. 1295-1301; doi:10.1080/14656566.2016.1183647.
Vichai, et al: "Sulforhodamine B colorimetric assay for cytotoxicity screening", Protocol; Aug. 17, 2006; vol. 1, No. 3, pp. 1112-1116.
Shukla, et al: "Current and Emerging Therapeutic Strategies for Fanconi anemia", The Hugo Journal 2012; vol. 6(1),pp. 1-8.
Bito, Toshinori et al., "Inhibition of Epidermal Growth Factor Receptor and PI3K/Akt Signaling Suppresses Cell Proliferation and Survival through Regulation of Stat3 Activation in Human Cutaneous Squamous Cell Carcinoma", *Hindawi Publishing Corporation, Journal of Skin Cancer*, vol. 2011, Article ID 874571; 11 pages (doi:10.1155/2011/874571).
Flatt, Terrie et al., "Successful Treatment of Fanconi Anemia and T-Cell Acute Lymphoblastic Leukemia", *Hindawi Publishing Corporation Case Reports in Hematology*, vol. 2012, Article ID 396395; 4 pages (doi: 10.1155/2012/396395).
Huang, Peixin et al., "The role of EGF-EGFR signalling pathway in hepatocellular carcinoma inflammatory microenvironment", *J. Cell. Mol. Med.*, vol. 18, No. 2, 2014; pp. 218-230.
Soria, Jean-Charles et al., "Afatinib versus erlotinib as second-line treatment of patients with advanced squamous cell carcinoma of the lung (LUX-Lung 8): an open-label randomised controlled phase 3 trial", *The Lancet Oncolgy*, vol. 16(8), Aug. 2015; pp. 897-907 (doi: 10.1016/S1470-2045(15)00006-6).
Wang, Xiao-kun et al., "Afatinib Enhances the Efficacy of Conventional Chemotherapeutic Agents by Eradicating Cancer Stem-like Cells", *Cancer Research, Therapeutics, Targets, and Chemical Biology*, 74(16), Aug. 15, 2014; pp. 4431-4445.

*Primary Examiner* — Golam M Shameem
(74) *Attorney, Agent, or Firm* — Squire Patton Boggs (US) LLP

(57) ABSTRACT

The present invention provides the afatinib or a pharmaceutically salt thereof for use in the treatment and/or prevention of a cancer in a patient suffering from a disease caused by a defect in DNA damage repair mechanism. Surprisingly, when afatinib was administered to FA cells, it was confirmed that there was a therapeutic anti-cancer effect without any toxic side-effect on DNA.

15 Claims, 4 Drawing Sheets

(A)

(B)

(A)

FIG. 2 (continuation)
(B)
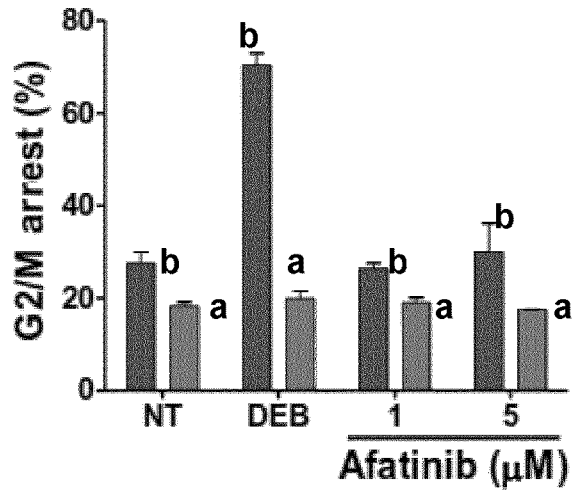
FIG. 3
(A)
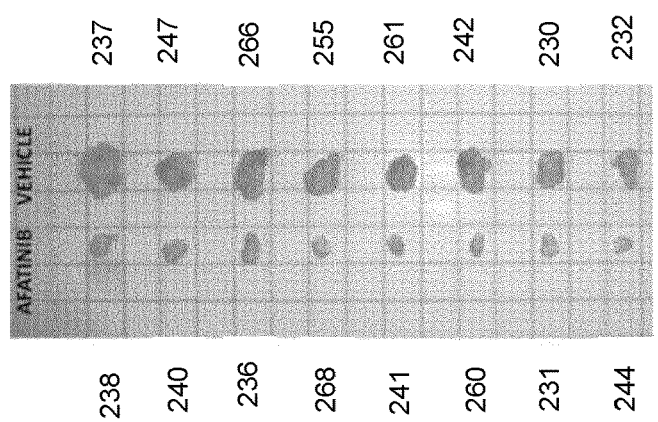
(B)
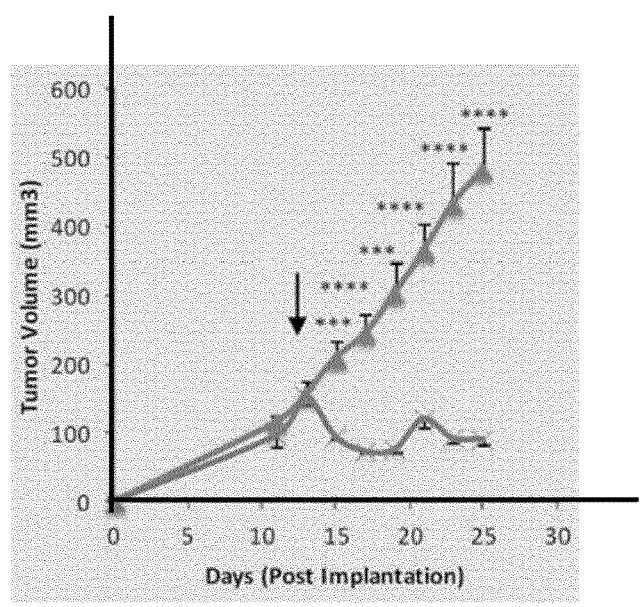

FIG. 3 (continuation)
(C)
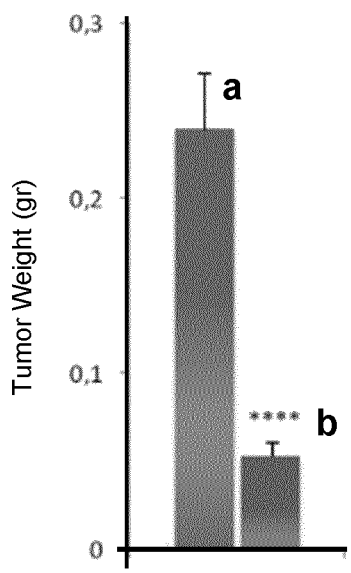
FIG. 4
(A)
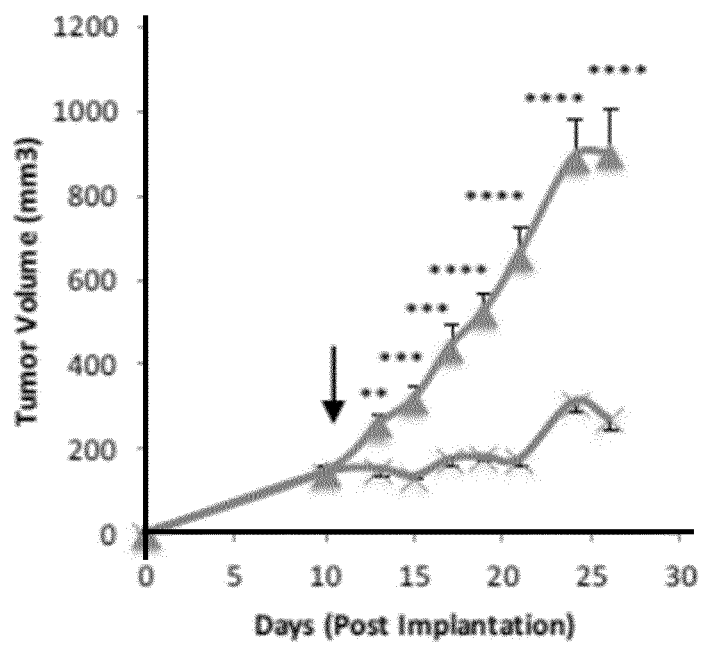

FIG. 4 (continuation)
(B)
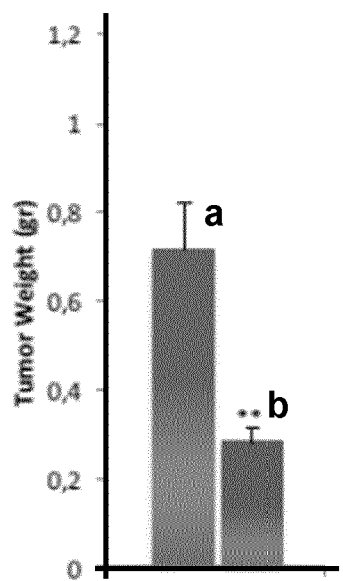
FIG. 5
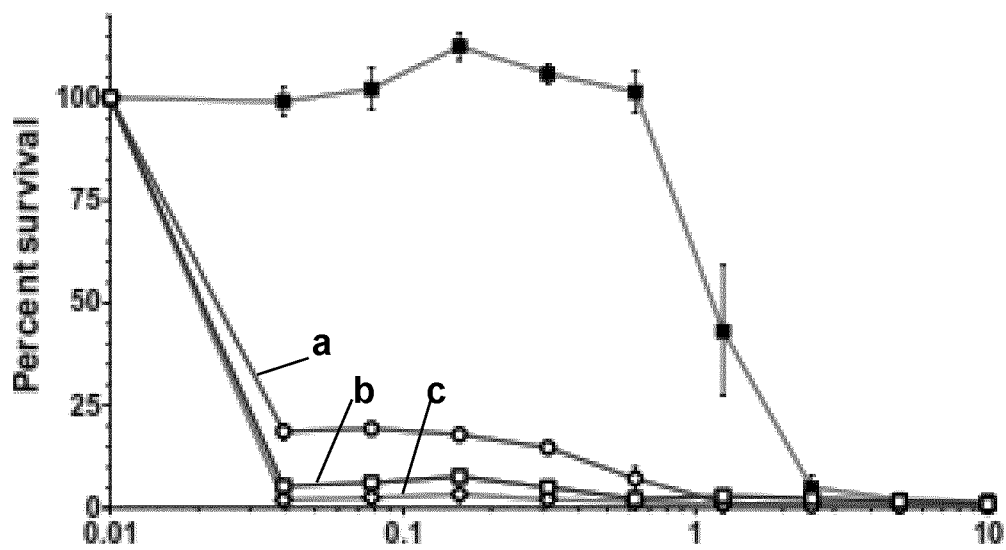

THERAPEUTIC USE OF AFATINIB IN CANCER

CROSS REFERENCE TO RELATED APPLICATIONS

This application is a national stage entry of PCT/EP2019/069039 filed, which claims the benefit of European Patent Application EP18382527.2 filed Jul. 16, 2018, and the contents of both of which are incorporated by reference in their entireties.

TECHNICAL FIELD

The present invention belongs to the field of medicine. In particular, the invention provides the use of afatinib in the treatment of cancer, particularly of a squamous cell carcinoma, in a subject suffering a disease caused by a defect in DNA damage repair mechanism.

BACKGROUND ART

The human genome is constantly exposed to various sources of DNA damage and our organism commands a number of highly conserved and effective mechanisms responsible for DNA repair. If these repair mechanisms are defective due to mutations in relevant genes, diseases with DNA repair deficiencies can arise.

Today, there are a number of diseases characterized by genetic defects in DNA repair mechanisms, such as Ataxia telangiectasia, Nijmegen breakage syndrome, Werner syndrome, Seckel syndrome, Bloom syndrome, Fanconi anemia, Xeroderma pigmentosum, Cockayne syndrome, trichothiodystrophy, among others. Although heterogeneous in respect to symptoms, these rare disorders share many clinical features such as bone marrow failure, growth retardation, neurological disorders, premature ageing, skin conditions including abnormal pigmentation, telangiectasia, xerosis cutis, pathological wound healing as well as an increased risk of developing different types of cancer.

Fanconi's anemia (FA) is a rare autosomal recessive disorder that is characterized by developmental anomalies, growth retardation and progressive bone marrow failure. FA patients frequently show cytogenetic abnormalities as well as defects in the DNA repair mechanism.

Much effort is being made on Fanconi anemia therapeutics to treat bone marrow failure, one of the main and most life threatening signs of the disease. And as mortality rate by bone marrow failure has been dramatically reduced in the last years, thanks to improved hematopoietic stem cell transplantation protocols, and with the promise of improved approaches such as gene therapy, the next step in the horizon of Fanconi anemia treatment has to be focused on malignancies, which is the main related complication. FA patients have very low survival rate after solid tumors appear. Recent reports support the recorded high incidence of squamous cell carcinoma in these cases, and especially for tumor in the head and neck area. However, hepatocellular carcinomas associated with anabolic steroids have also been reported in the patients suffering FA.

Head and neck squamous cell carcinomas (HNSCCs) are the most common solid tumour in individuals with FA. The incidence is 500- to 700-fold higher than in the general population. The incidence of solid tumors is around 30% at 40 years, being 50% head and neck squamous cell carcinomas.

The HNSCCs in FA show distinct differences compared to HNSCCs seen in the general population. HNSCCs:
- Occur at an earlier age (20-40 years) than in the general population;
- Are most commonly in the oral cavity (e.g., tongue); and
- Present at an advanced stage.

In addition to the above, individuals with FA are at increased risk for second primary cancers in the skin and genitourinary tract. Even individuals with FA receiving androgen treatment for bone marrow failure are also at increased risk for liver tumour.

At present, cancer malignancies can be managed in these subjects by surgery. Traditional chemotherapy or radiotherapy has almost been disregarded in FA patients because they are extremely sensitive to treatment's toxicity. One of the main reasons for such sensitivity in FA patients is that current therapies can negatively affect (modify) the DNA, and in diseases such as FA, wherein the DNA repair mechanism is damaged, this can mean the onset of a further medical complication.

In view of the above, there is the need of a non-toxic efficient anti-cancer therapy for patients suffering a disease caused by a defect in DNA damage repair mechanism, such as Fanconi anemia.

SUMMARY OF INVENTION

The present inventors have surprisingly found that afatinib efficiently inhibits growth of head and neck squamous carcinoma in FA model mouse xenografts without causing toxic side-effects Fanconi anemia cells.

As it is shown below, inventors firstly evaluated the effect of afatinib in the DNA from cells whose DNA machinery worked correctly. With this aim, they evaluated whether afatinib activated FANCD2 ubiquitination, as an indirect measure of FA/BRCA pathway activation. As it is shown in FIGS. 1(A) and (B), no activation was detected, which means that even using high concentrations of afatinib (10 µM), no DNA damage (such as ICLs, stalled replication forks or DSBs) occurs.

In view of such promising results, the inventors further evaluated the effect of afatinib in the DNA from FA cells, wherein the DNA repair damage machinery does not correctly work. With this aim, they evaluated whether afatinib induced micronuclei formation or G2/M cell cycle arrest. As it is shown in FIGS. 2(A) and (B), no induction of micronuclei formation nor G2/M arrest in FA lymphoblastoid cell lines was detected, even using high concentrations of afatinib (10 µM).

Therefore, from these experimental data the first conclusion was that afatinib did not give rise to any DNA-based toxic side-effect in models suffering from a disease caused by a defect in the DNA repair damage machinery.

The inventors also found that such "innocuous effect" of afatinib administration in the DNA of FA cells did not diminish, at any extent, its effect as antitumoral agent. As it is shown below, the oral administration of afatinib to two FA-derived HNSCC cell lines in immunodeficient mice models (one induced injecting the cell line 1604 and the other injecting the cell line 1131) remarkably reduced the tumor size (FIGS. 3A-3B, and 4A-4B).

In addition to the above, it was also found that afatinib was highly selective of tumor cells vs non-tumor cells (see FIG. 5).

Altogether, these results support the use of afatinib as a safe and efficient therapy for a cancer in a subject of patients suffering from a disease caused by a defect in DNA damage repair mechanism.

The present invention means a great advance in the treatment of cancer in this population of patients which, up to now, had only the surgical resection as main anti-cancer therapeutic approach due to the several DNA toxic side-effects of chemo- or radiotherapy.

In view of the above, the present invention provides the afatinib or a pharmaceutically salt thereof for use in the treatment and/or prevention of cancer in a subject suffering a disease caused by a defect in the DNA damage repair mechanism. This aspect can also be formulated as the use of afatinib or a pharmaceutically salt thereof for the manufacture of a medicament for the treatment and/or prevention of cancer in a patient suffering a disease caused by a defect in the DNA damage repair mechanism. This aspect can also be formulated as a method for the treatment and/or prevention of cancer in a patient suffering a disease caused by a defect in the DNA damage repair mechanism, the method comprising the step of administering a therapeutically effective amount of afatinib or a pharmaceutically salt thereof to the patient in need thereof.

BRIEF DESCRIPTION OF DRAWINGS

FIG. 3: afatinib inhibit growth of FA 1604 HNSCC cell line in vivo in mouse xenograft experiments (A) Excised tumors at end-point. Numbers indicate animal ID. (B) Tumor volume: values represented as triangles correspond to the tumor volume in the FA model with no afatinib treatment. The arrow indicates the start of the treatment. The values represented as crosses correspond to the tumor volume once administered the drug. (C) Tumor weight mean at end-point of the assay: "a"-bar corresponds to the group which did not receive afatinib; "b"-bar corresponds to the group which received afatinib.

FIG. 4: afatinib inhibits growth of FA 1131 HNSCC cell line in vivo in mouse xenograft experiments. (A) Tumor volume: values represented as triangles correspond to the tumor volume in the FA model with no afatinib treatment. The arrow indicates the start of the treatment. The values represented as crosses correspond to the tumor volume once administered the drug. (B) Tumor weight mean at end-point of the assay: "a"-bar corresponds to the group which did not receive afatinib; "b"-bar corresponds to the group which received afatinib.

FIG. 5: Survival assays in FA cells (FA551, primary fibroblasts; black square) and three different FA HNSCC cell lines for afatinib (1365 (line "a"), 1131 (line "b") and 1604 (line "c")). Ratio of non tumoral vs tumoral $IC_{50}$ is about 340.1.

DETAILED DESCRIPTION OF THE INVENTION

Figure 1:
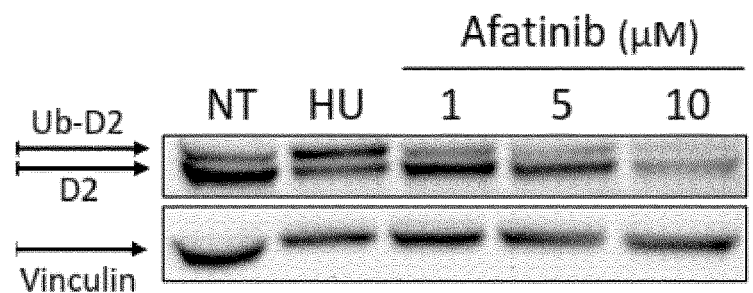
FIG. 1: (A) U2OS cells were stimulated over night with different concentrations of afatinib or 2 mM HU (as a positive control). Cells were lysed and FANCD2 ubiquitination analyzed by Western blot. Vinculin was used as a loading control. (B) shows averaged graph of the independent experiment of cells treated with afatinib, respectively. Y-axis represents the % of ubiquitination vs non-ubiquitination at different afatinib concentrations.
Figure 1:
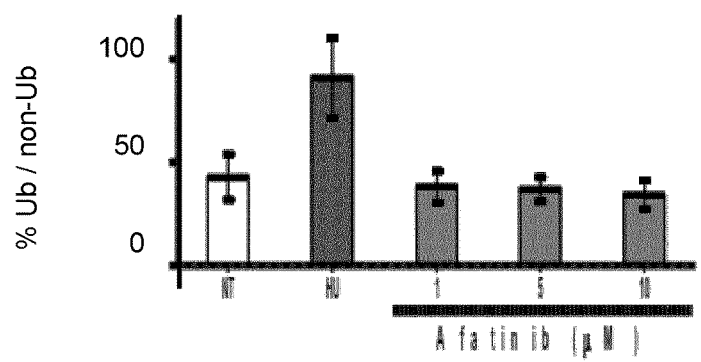

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

As mentioned above, the present invention provides the afatinib or a pharmaceutically salt thereof for use in the treatment and/or prevention of cancer in a subject suffering a disease caused by a defect in DNA damage repair mechanism Afatinib is the International Nonproprietary Name (INN) of (E)-N-[4-(3-chloro-4-fluoroanilino)-7-[(3S)-oxolan-3-yl]oxyquinazolin-6-yl]-4-(dimethylamino)but-2-enamide and has the CAS number 850140-72-6. Afatinib has the formula (I):

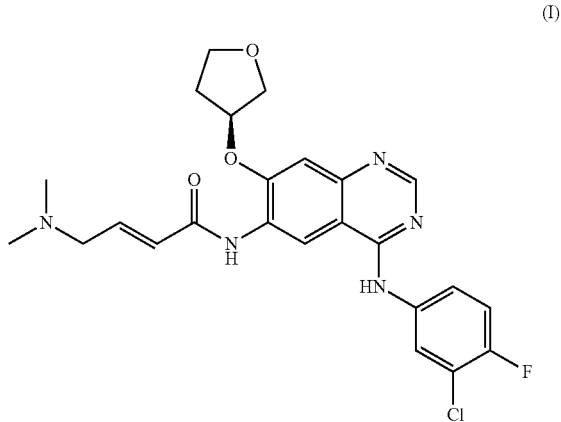 [SMILES: CN(C)C/C=C/C(=O)Nc1cc2c(Nc3ccc(F)c(Cl)c3)ncnc2cc1O[C@H]1CCOC1]

(I)

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutical acceptable salts are well known in the art. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, trifluoroacetic acid, oxalic acid, maleic acid, tartaric acid, citric acid, succinic acid or malonic acid or by using other methods used in the art such as ion exchange. Other pharmaceutical acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, and ammonium. Representative alkali or alkaline earth metal salts include sodium, lithium, potassium, calcium, magnesium, and the like. Further pharmaceutical acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

The skilled person is able to prepare afatinib's pharmaceutically acceptable salts following routine methods.

In the present invention the expression "disease caused by a defect in DNA damage repair mechanism" refers to any condition caused by a reduced functionality of the cellular DNA repair machinery. The defect in the DNA damage repair mechanism is usually due to genetic mutations. Depending on the particular mutations, the disease can comprise at least one of the following symptoms: growth retardation, neurological disorders, premature ageing, pathological wound healing, skin condition or hematological dysfunction, among others.

In the present invention, the term "growth retardation" refers to developmental abnormalities, mental retardation and/or psychomotor retardation.

In the present invention, the term "premature aging" means that the aging process, due to mutations in DNA repair machinery, is accelerated. As a consequence of this acceleration the resulting cell/tissue has physical features which do not correspond to the actual age of the subject but to an older stage.

In the present invention, the term "skin condition" refers to a non-healthy skin state, for example, a dry skin due to rough skin, dry skin, loose and wrinkles, spots, freckles or skin diseases caused by active oxygen, and the like. In one embodiment, the skin condition is abnormal pigmentation.

In the present invention, the term "hematological dysfunction" refers to a failure in one or more of the organs forming part of the hematologic system such as bone marrow, thymus or secondary lymphatic organs (such as spleen, MALT, liver and lymph nodes). Organ(s) failure gives rise to an alteration in the levels of one or more of the cellular components forming part of the blood, such as erythrocytes, leukocytes, and platelets, coagulation factors, natural antithrombotics, and proteins of the fibrinolytic system. In one embodiment, the hematological dysfunction is due to a bone marrow failure, which gives rise to a dramatically reduced concentration of erythrocytes.

In an embodiment, the disease caused by a defect in DNA damage repair mechanism is selected from the group consisting of Ataxia telangiectasia, Nijmegen breakage syndrome, Bloom syndrome, Cockayne syndrome, Fanconi anemia, Hutchinson Gilford progeria, Rothmund Thomson syndrome, trichothiodystrophy, Werner syndrome and Xeroderma pigmentosum. In another embodiment, optionally in combination with any of the embodiments provided below, the disease is Fanconi anemia.

In another embodiment, optionally in combination with any of the embodiments provided above or below, the cancer is selected from leukemia (myeloid leukemia), squamous cell carcinoma (oral, esophageal, or vulvar), and hepatocellular carcinomas. In yet another embodiment, optionally in combination with any of the embodiments provided above or below, the cancer is squamous cell carcinoma. In yet another embodiment, optionally in combination with any of the embodiments provided above or below, the cancer is head and neck squamous cancer.

In one embodiment, optionally in combination with any of the embodiments provided above or below, the invention refers to the use of afatinib or the pharmaceutically salt thereof in the treatment and/or prevention of a squamous cell carcinoma or hepatocellular carcinoma in a FA patient. In another embodiment, optionally in combination with any of the embodiments provided above or below, the invention refers to the use of afatinib or the pharmaceutically salt thereof in the treatment and/or prevention of a squamous cell carcinoma in a FA patient. In another embodiment, optionally in combination with any of the embodiments provided above or below, the invention refers to the use of afatinib or the pharmaceutically salt thereof in the treatment and/or prevention of a head and neck squamous cell carcinoma in a FA patient.

In one embodiment, optionally in combination with any of the embodiments provided above or below, the invention refers to the use of such as afatinib dimaleate (CAS Number 850140-73-7) in the treatment and/or prevention of a squamous cell carcinoma or hepatocellular carcinoma in a FA patient. In another embodiment, optionally in combination with any of the embodiments provided above or below, the invention refers to the use of such as afatinib dimaleate in the treatment and/or prevention of a squamous cell carcinoma in a FA patient. In another embodiment, optionally in combination with any of the embodiments provided above or below, the invention refers to the use of such as afatinib dimaleate in the treatment and/or prevention of a head and neck squamous cell carcinoma in a FA patient.

In another embodiment, optionally in combination with any of the embodiments provided above or below, afatinib or the pharmaceutically salt thereof is administered in a therapeutically effective amount in the form of a pharmaceutical composition, together with one or more pharmaceutically acceptable excipients and/or carriers.

The expression "therapeutically effective amount", as used herein, refers to the amount of afatinib or pharmaceutically salt thereof that, when administered, is sufficient to prevent development of, or alleviate to some extent, one or more of the symptoms of the disease which is addressed. The particular dose of agent administered according to this invention will of course be determined by the particular circumstances surrounding the case, including the route of administration, the particular condition being treated, and similar considerations.

The expression "pharmaceutically acceptable excipients and/or carriers" refers to pharmaceutically acceptable materials, compositions or vehicles. Each component must be pharmaceutically acceptable in the sense of being compatible with the other ingredients of the pharmaceutical composition. It must also be suitable for use in contact with the tissue or organ of humans and non-human animals without excessive toxicity, irritation, allergic response, immunogenicity or other problems or complications commensurate with a reasonable benefit/risk ratio. Examples of suitable pharmaceutically acceptable excipients are solvents, dispersion media, diluents, or other liquid vehicles, dispersion or suspension aids, surface active agents, isotonic agents, thickening or emulsifying agents, preservatives, solid binders, lubricants and the like. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

The pharmaceutical composition provided by the present invention may be oral.

It is clear for the skilled person that the composition may be prepared using state of the art excipients and applying usual pharmaceutical technologies.

The dosage form may be, for instance, a solid pharmaceutical composition such as tablets or coated tablets, powders, fine granules, granules, capsules e.g. hard or soft gelatin capsules, troches (pastilles), a bolus and chewable preparations containing afatinib or a pharmaceutically acceptable salt thereof.

The preparation of pharmaceutical forms of the above-mentioned kind is well-known per se from the prior art. The dose of afatinib or pharmaceutically acceptable salt containing composition of the invention to be administered may appropriately be controlled depending on the dosage forms of the desired pharmaceutical preparations.

The afatinib containing pharmaceutical composition of the invention may be administered to a patient in a daily dose in portions over one or several times per day if it is in the dosage form of an orally administered solid preparation such as a tablet or an orally or parenteral liquid preparation.

The amount of the effective substance may also be formulated into a single dose, in as much as it is not unreasonable from the viewpoint of the dosage form of the pharmaceutical preparation.

In one embodiment, optionally in combination with any of the embodiments provided above or below, the solid dosage form such as a capsule, tablet, pastille, granule, a powder or a liquid or another dosage form for oral application may contain afatinib or a pharmaceutically acceptable salt thereof, such as afatinib dimaleate, in an amount allowing to provide 10 to 60 mg or 20 to 50 mg of the active ingredient per single dose. In one embodiment, optionally in combination with any of the embodiments provided above or below, the solid dosage form such as a capsule, tablet, pastille, granule, a powder or a liquid or another dosage form for oral application may contain afatinib or a pharmaceutically acceptable salt thereof, such as afatinib dimaleate, in an amount allowing to provide 20, 30, 40 or 50 mg of the active ingredient per single dose. The AEMP's authorization provides also detail information about particular doses, routes and pharmaceutical compositions.

In the preparation of the afatinib containing composition, a variety of currently used additives may be employed, such as one or more of a filler, a thickening agent, a gelling agent, a binder, a disintegrator, a surfactant, a lubricant, a coating agent, a sustained release agent, a diluent and/or one or more excipients. In addition to the foregoing, the agent of the present invention may, if necessary, further comprise other additives such as a solubilizing agent, a buffering agent, a preservative, an isotonic agent, an emulsifying agent, a suspending agent, a dispersant, a hardening agent, an absorbent, an adhesive, an elasticizing agent, an adsorbent, a perfume, a coloring agent, a corrigent, an antioxidant, a humectant, a light-screening agent, a brightener, a viscosity enhancer, an oil, a tableting adjuvant, and/or an anti-static agent.

Suitable pharmaceutically acceptable excipients include, but are not limited to, diluents such as mannitol, dextrose, lactose, lactose anhydrous, microcrystalline cellulose, starch, pregelatinized starch, and lactitol.

The composition may further, include, disintegrants, such as croscarmellose sodium, crospovidone, sodium starch glycolate, polacrilin potassium, pregelatinized starch and the like and mixtures thereof.

Other categories of excipients such as lubricants, glidants may be included in the solid oral dosage form of the present invention.

The solid oral dosage form is packed in a container together with a moisture resistant means such as desiccant.

Moreover, it is also possible to prepare coated pharmaceutical preparations through the use of a currently used coating agent such as hydroxypropyl methyl cellulose, hydroxypropyl cellulose, methyl cellulose or polyvinyl pyrrolidone.

If necessary, a non-toxic FA sweetener may likewise be used, such as in troches, syrups and chewable preparations among others.

As non-toxic FA solubilisers any known solubiliser suitable in the medical sector may be used, for example polyethyleneglycols, polyoxyethylene-polyoxypropylene copolymers (e.g. poloxamer 188), glycofurol, arginine, lysine, castor oil, propyleneglycol, solketal, polysorbate, glycerol, polyvinyl pyrrolidone, lecithin, cholesterol, 12-hydroxystearic acid-PEG660-ester, propyleneglycol monostearate, polyoxy-40-hydrogenated castor oil, polyoxyl-10-oleyl-ether, polyoxyl-20-ceto-stearylether and polyoxyl-40-stearate or a mixture thereof.

Any non-toxic FA preservative known for use in the pharmaceutical field may be used, for example, benzoic acid and the sodium or potassium salts thereof, sorbic acid and the sodium or potassium salts thereof, among others.

The buffer system used to achieve a desired pH value may be, for example, glycine, a mixture of glycine and HCl, a mixture of glycine and sodium hydroxide solution, and the sodium and potassium salts thereof, a mixture of potassium hydrogen phthalate and hydrochloric acid, a mixture of potassium hydrogen phthalate and sodium hydroxide solution or a mixture of glutamic acid and glutamate.

Suitable gelling agents are for example cellulose and its derivatives, like for instance methyl cellulose, carboxymethyl cellulose, hydroxypropylmethyl cellulose, poly(vinyl) alcohol, polyvinylpyrrolidones, polyacrylates, poloxamers, tragacanth, carrageenan, starch and its derivatives or any other gelling agent used in pharmaceutical technology.

Viscosity enhancers which may be mentioned are for example the aforementioned gelling agents in low quantities, glycerol, propylene glycole, polyethylene glycol or polyols, like sorbitol and other sugar alcohols.

The emulsifiers used, apart from the emulsifiers known from the prior art, may include polyoxyethylene derivatives of castor oil or polyoxyethylene alkylethers.

Suitable synthetic or natural, coloring agents known in the pharmaceutical field may be used such as Indigo carmine.

Suitable oily components which may be present are any of the oily substance known from the prior art for the preparation of pharmaceuticals, such as, for example, vegetable oils, in particular, e.g. cotton seed oil, groundnut oil, peanut oil, maize oil, rapeseed oil, sesame oil and soya oil, or triglycerides of moderate chain length, e.g. fractionated coconut oil, or isopropylmyristate, -palmitate or mineral oils or ethyloleate.

The antioxidants used may be any of the antioxidants known from the prior art, for example a-tocopherol, butylhydroxytoluene (BHT) or butylhydroxyanisole (BHA).

Pharmaceutical compositions containing these additives may be prepared according to any method known in this field, depending on the dosage form. It is a matter of course that further additives not explicitly discussed may be used in the formulations used according to the present invention.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Reference signs related to drawings and placed in parentheses in a claim, are solely for attempting to increase the intelligibility of the claim, and shall not be construed as limiting the scope of the claim. Furthermore, the present invention covers all possible combinations of particular and preferred embodiments described herein.

EXAMPLES

Cell Lines and Reagents

FANCA-deficient (FA551) primary fibroblasts, U2OS, HNSCC VU040-T (WT), VU1131-T2.8 (FANCC$^{-/-}$), VU1604-T (FANCL$^{-/-}$) and VU1365-T (FANCA$^{-/-}$) cell lines, were grown in DMEM (Biowest) supplemented with 10% heat inactivated FBS and plasmocin (ant-mpt, Invivogen).

Lymphoblastoid cell line LFA139 comes from a healthy donor, LFA55 come from a Fanconi anemia patient with biallelic mutations in FANCA gene. This cell line is available in the Department of Genetics and Microbiology of Universitat Autonoma de Barcelona. Lymphoblastoid cell lines were grown in RPMI medium supplemented with 20% heat inactivated FBS, penicillin-streptomycin, sodium privuate, non essential aminoacids and β-mercaptoethanol, and maintained between $0,5-1,5\times10^6$ cells per mililiter.

HNSCCs were kindly provided by Dr Josephine Dorsman. Ethidium Monoazide Bromide (EMA) was from ThermoFischer Scientific (Cat. N°. e1374).

IGEPAL was from Sigma (Cat. N° 18896). RNAse A was from Invitrogen (Cat. N° 12091021). Mitomycin C (MMC, ref. M-0503), DAPI (Cat. N° D9542), sulforhodamine B (ref. S1402), trichloracetic acid (ref. T6399) and β-escin (E1378) were from Sigma. afatinib dimaleate(11492) was from Cayman Chemical.

Survival Assay

In antitumoral validation, cells were seeded in sextuplicates in 96 well plates and left untreated 24 hours. Cultures were then exposed to 9 different concentrations of MMC or afatinib, left 7 days and stained and measured with sulforhodamine B (SRB) assay (Vichai, V. et al., 2006). Briefly, cells were fixed with 30% trichloroacetic acid (TCA) for 1 hour at room temperature (RT), plates washed with distilled water and dried. Fixed cells were dyed with 40 mL/well of 0,4% SRB in 1% acetic acid for 30 minutes at RT. Plates were then washed in 1% acetic acid solution, dried, and SRB fixed in cells dissolved in 200 mL/well of 10 mM Tris pH 10. Absorbance at 495 nm was measured in a microplate reader (Sunrise, Tecan). Cell viability was measured applying the following equation: $(OD_{495}$ treated cells$-OD_{495}$ medium$)/(OD_{495}$ control cells$-OD_{495}$ medium$)*100$ $IC_{50}$ of afatinib was determined by calculating logarithmic trend lines with GraphPad. It was also calculated the ratio from $IC_{50}$ of non tumoral cell lines (primary fibroblasts) vs averaged $IC_{50}$ of the three FA HNSCC cell lines (FIG. 5).

Western Blot

U2OS and HNSCCs cell lines were lysated with Radioimmunoprecipitation assay buffer (RIPA buffer, 20-188, Millipore), supplemented with protease inhibitors (04693159001, Sigma), phosphatase inhibitors (04906837001, Sigma) and benzonase (70746, Novagen) and sonicated (Branson 250).

Western blot was performed to detect expression of FANCD2 (Ab2187 from Abcam), and Vinculin (Ab18058 from Abcam).

In Vitro Flow Cytometric Micronuclei (FCM) Assay

FCM assay was described earlier (Bryce S. M. et al., 2007; Avlasevich S. et al., 2011). Briefly, 60.000 cells/well were plated using 96 well plates in a total volume of 120 µL/well. Cells were then treated with diepoxybuthane (DEB, 0.1 µg/ml) or afatinib for 3 days. After treatment cells were centrifuged at 800 rpm for 8 min. Supernatant was removed and cells were resuspended by vortexing. 62.5 µL of EMA solution (0.125 mg/mL in PBS with 2% of FBS) was added to cell suspension. For the photo-activation step, plates were placed on ice under the visible light from a light bulb located 30 cm above the cells for 20 min. After the photo-activation step (EMA covalently binds the DNA of cells with disrupted membrane integrity-dead/dying cells), plates were protected from light exposure for the remaining steps of the staining procedure. 200 µL of cold PBS with 2% FBS were added and cells were centrifuged at 800 rpm for 8 min. Supernatant was discarded and cells were resuspended by vortexing. Cell suspension was kept at room temperature for 20 minutes before cell lysis. Cells were then lysed in a two-step procedure. 100 µL of lysis solution 1 (0.584 mg/mL NaCl, 1 mg/mL sodium citrate, 0.3 µL/mL IGEPAL, 1 mg/mL RNase A, 1 µg/mL DAPI) were added. Samples were incubated at room temperature for 1 h. After the incubation, 100 µL of lysis solution 2 (85.6 mg/mL sacarose, 15 mg/mL citric acid and 1 µg/mL DAPI) were added into the samples and immediately vortexed. Samples were incubated at room temperature for 30 min and were stored into a cold chamber overnight until the specimens were measured. Flow cytometry analysis was performed with a FACS Fortessa cytometer.

At least 20,000 EMA negative-DAPI positive events (divided nuclei) were gated per sample. 3 replicates per condition were analysed. To exclude events that were not MN or nucleus from live cells, different gates were used for analysis that includes forward scatter, side scatter, DAPI and EMA fluorescence.

Micronuclei frequency was expressed as the number of micronuclei per thousand nuclei obtained. Percentage of cells arrested in G2/M phase was obtained in the plot with nuclei.

In Vivo Xenograft Experiments

NOD-SCID mice (both sexs, age ranging from 6 weeks to 9 week-old) were injected subcutaneously with a mixture 1:1 of $1\times10^6$ VU1131 or VU1604 cells: matrigel in the right flank.

Animals were monitored twice a week (weight and tumor volume) until tumors were $\approx150$ mm$^3$. Eleven days post-inoculation, animals were randomized (tumor volume and sex) into 4 experimental groups and started to receive treatment (n=8 animals/group): 11) Vehicle (Methylcellulose); 2) Afatinib. Afatinib-based treatment (20 mg/kg) was administered 5 days a week orally (gavage) for about 2 weeks.

Animals were monitored three times a week (body weight and tumor volume) until tumors were $\approx1000$ mm$^3$. At end-point, animals were euthanized and tumors were surgically removed. Tumor specimens were processed to establish FFPE (Formalin-Fixed Paraffin-Embedded) and frozen (−80° C.) samples.

In Vivo Toxicity Experiments

The generation of mice with a targeted disruption in the Fanconi anemia A gene has been previously described (Rio P. et al., 2002). Wild type and FANCA-deficient mice (female, age ranging from 8 to 20 weeks) were weight randomized into 2 experimental groups and started to receive treatment (n=6 animals/group):1) Vehicle (Methylcellulose); 2) Afatinib. Afatinib-based treatment (20 mg/kg) was administered 5 days a week orally (gavage), for two weeks.

Animals were monitored three times a week (body weight), and tail bleeded at 0 (pretreatment), 7 and 14 days (end-point) of treatment.

At end-point, animals were euthanized and bone marrow from femurs extracted for further analysis.

Results

Afatinib does not Activate Fanconi Anemia Pathway

To discard a direct toxic effect on DNA that could dampen their use in FA patients, U2OS cells were treated with afatinib to analyze FA/BRCA pathway by FANCD2 ubiquitination. As seen in FIGS. 1A and 1B, afatinib does not activate FANCD2 ubiquitination, and thus FA/BRCA pathway, up to at 10 µM, suggesting that it does not induce ICLs, stalled replication forks or DSBs on DNA.

Figure 2:
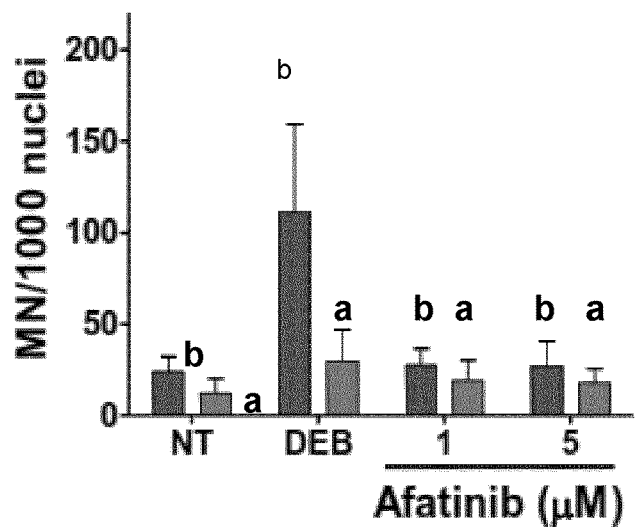
FIG. 2: (A) WT ("a"-marked bars) and FA-derived ("b"-marked bars) lymphoblastoid cell lines were used to analyze formation of micronuclei by flow cytometry micronucleus assay with different concentrations of afatinib. (B) shows G2/M cell cycle arrest, with different concentrations of afatinib. Diepoxybutane (DEB) was used as a positive control. Bars show mean+/−SEM of three independent experiments with similar results.

When assessing its capacity to induce micronuclei or G2/M cell cycle arrest in FA cells, which are highly sensitive to ICLs such as diepoxybutane, it was found that high doses of afatinib (10 µM) were unable to induce micronuclei nor G2/M arrest in WT or FA lymphoblastoid cell lines, further discarding a toxicity effect targeting DNA (FIGS. 2A and 2B).

Afatinib Inhibits Growth of FA HNSCCs in Mouse Xenografts

To check more physiologically the effect of afatinib on FA HNSCC growth, xenograft experiments were carried out in NOD-SCID immunodeficient mice.

HNSCC cells were injected subcutaneously in the right flank of mice, and once they reached an average size of 150 mm$^3$ drug treatment was given orally five times a week. It was found that 1604 grew very quickly in control groups in just two weeks. Afatinib treatment could efficiently inhibit growth of both HNSCC cell lines. Best results were obtained with 1604 HNSCC, where the drug could inhibit tumor size in all mice, giving partial response in 7/8 mice and stable disease in 1/8 (FIGS. 3A and 3B). In 1131 HNSCC, it was found that this cell line grew at a much higher rate and tumor size at the end point was two times bigger than with 1604 HNSCC cells (FIGS. 4A and 4B).

In summary, these results allow concluding that afatinib can inhibit the proliferation of squamous cancer cells without inducing toxicity in FA cell lines, nor activating FA/BRCA pathway nor producing chromosomic fragility.

Altogether, these results support the use of afatinib as a safe and efficient therapy for HNSCC in Fanconi anemia, that could efficiently improve the natural history of this rare disease.

CITATION LIST

Avlasevich S. et al., "Flow cytometric analysis of micronuclei in mammalian cell cultures: past, present and future", 2011, Mutagenesis, 26, 147-152;

Bryce S. M. et al., "In vitro micronucleus assay scored by flow cytometry provides a comprehensive evaluation of cytogenetic damage and cytotoxicity", 2007, Mutat. Res. Toxicol. Environ. Mutagen., 630, 78-91;

Rio P. et al., "In vitro phenotypic correction of hematopoietic progenitors from Fanconi anemia group A knockout mice", 2002, Blood, 100, 2032-9;

Vichai V. et al., "Sulforhodamine B colorimetric assay for cytotoxicity screening", 2006, Nat. Protoc., 1, 1112-6;

The invention claimed is:

1. A method for the treatment of cancer, wherein the cancer is selected from leukemia, a squamous cell carcinoma, and hepatocellular carcinoma, in a patient suffering from a disease caused by a defect in DNA damage repair mechanism, wherein the disease is Fanconi anemia, the method comprising administering a therapeutically effective amount of afatinib or a pharmaceutical salt thereof to the patient in need thereof.

2. The method according to claim 1, wherein the cancer is selected from a squamous cell carcinoma and hepatocellular carcinoma.

3. The method according to claim 1, wherein the cancer is a squamous cell carcinoma.

4. The method according to claim 3, wherein the cancer is a head and neck squamous cell carcinoma.

5. The method according to claim 1, wherein the afatinib or a pharmaceutical salt thereof is administered in the form of a pharmaceutical composition, together with one or more pharmaceutically acceptable excipients and/or carriers.

6. The method according to claim 5, wherein the pharmaceutical composition is an oral pharmaceutical composition.

7. The method according to claim 1, wherein a therapeutically effective amount of an afatinib salt is administered, and the afatinib salt is afatinib dimaleate salt.

8. The method according to claim 7, wherein the afatinib dimaleate salt is administered in the form of a pharmaceutical composition.

9. The method according to claim 3, wherein the afatinib or a pharmaceutical salt thereof is administered in the form of a pharmaceutical composition, together with one or more pharmaceutically acceptable excipients and/or carriers.

10. The method according to claim 3, wherein the afatinib or pharmaceutical salt thereof is administered in the form of an oral pharmaceutical composition.

11. The method according to claim 3, wherein a therapeutically effective amount of an afatinib salt is administered, and the afatinib salt is afatinib dimaleate salt.

12. The method according to claim 11, wherein the afatinib dimaleate salt is administered in the form of a pharmaceutical composition.

13. The method according to claim 2, wherein the afatinib or a pharmaceutical salt thereof is administered in the form of a pharmaceutical composition, together with one or more pharmaceutically acceptable excipients and/or carriers.

14. The method according to claim 7, wherein the afatinib dimaleate salt is administered in the form of an oral pharmaceutical composition.

15. The method according to claim 11, wherein the afatinib dimaleate salt is administered in the form of a pharmaceutical composition and the pharmaceutical composition is an oral pharmaceutical composition.

* * * * *